United States Patent
Boye

(10) Patent No.: US 12,006,139 B2
(45) Date of Patent: Jun. 11, 2024

(54) DISPOSABLE PAD FOR INDOOR AND OUTDOOR GARBAGE CANS

(71) Applicant: Stellar Enterprise LLC, Oneida, WI (US)

(72) Inventor: Keith R. Boye, Oneida, WI (US)

(73) Assignee: Stellar Enterprise LLC, Oneida, WI (US)

( * ) Notice: Subject to any disclaimer, the term of this patent is extended or adjusted under 35 U.S.C. 154(b) by 298 days.

(21) Appl. No.: 17/496,920

(22) Filed: Oct. 8, 2021

(65) Prior Publication Data

US 2022/0112030 A1 Apr. 14, 2022

Related U.S. Application Data

(60) Provisional application No. 63/089,803, filed on Oct. 9, 2020.

(51) Int. Cl.
*B65F 1/06* (2006.01)
*A01N 25/10* (2006.01)
(Continued)

(52) U.S. Cl.
CPC ................ *B65F 1/06* (2013.01); *A01N 25/10* (2013.01); *A01N 25/34* (2013.01); *A01P 1/00* (2021.08);
(Continued)

(58) Field of Classification Search
CPC .... B65F 7/005; B65F 7/00; B65F 1/06; B65F 2210/129; A01P 1/00; A01N 25/10;
(Continued)

(56) References Cited

U.S. PATENT DOCUMENTS

| 1,131,102 | A | * | 3/1915 | Aldrich | B65F 1/1447 |
|---|---|---|---|---|---|
| | | | | | 220/908 |
| 1,724,579 | A | * | 8/1929 | Gunnell | B65F 7/00 |
| | | | | | 220/495.11 |

(Continued)

FOREIGN PATENT DOCUMENTS

| DE | 29916205 U1 * | 2/2001 | ................ B65F 1/02 |
|---|---|---|---|
| WO | WO-2005011757 A1 * | 2/2005 | ............. A01N 35/02 |
| WO | WO-2018002284 A1 * | 1/2018 | ............. A01N 25/34 |

OTHER PUBLICATIONS

Translation of DE29916205, Holter, Mar. 22, 2001, p. 3 (Year: 2001).*

(Continued)

*Primary Examiner* — Robert J Hicks
(74) *Attorney, Agent, or Firm* — Boyle Fredrickson, S.C.

(57) ABSTRACT

Systems and methods for sanitizing, cleaning, and deodorizing a garbage can are provided. The sanitization product can include a disposable pad covered in a solution that is inserted into indoor or outdoor garbage cans. The solution may be configured to minimize and prevent the spread of bacteria and other germs within a garbage can, which routinely occurs due to spilling of food, liquids, and other garbage within the can. Additionally, the pad may be made of an absorbable material so that any liquids that enter a garbage can can immediately be absorbed. Different solutions may be applied to the product depending on where the pad will be used. Additionally, a kit may be provided that includes multiple disposable pads. For instance, the kit may include a dozen pads, or more or less pads, that help to keep the user's garbage can clean and void of unpleasant odors.

19 Claims, 4 Drawing Sheets

(51) Int. Cl.
*A01N 25/34* (2006.01)
*A01P 1/00* (2006.01)
*A61L 2/18* (2006.01)
*A61L 2/26* (2006.01)
*A61L 9/012* (2006.01)

(52) U.S. Cl.
CPC ............... *A61L 2/18* (2013.01); *A61L 2/26* (2013.01); *A61L 9/012* (2013.01); *B65F 2210/1023* (2013.01); *B65F 2210/1026* (2013.01); *B65F 2210/129* (2013.01)

(58) Field of Classification Search
CPC .......... A01N 25/08; A01N 25/34; A61L 2/18; A61L 2/16; A61L 2/26; A61L 9/012; A61L 9/01; Y10S 220/9082; Y10S 220/9081; Y10S 220/908
USPC ........... 220/87.1, 908.2, 908.1, 908, 495.11, 220/495.08, 495.06; 422/1
See application file for complete search history.

(56) References Cited

U.S. PATENT DOCUMENTS

| | | | |
|---|---|---|---|
| 2,425,612 A | 11/1944 | Gamber | |
| 2,798,636 A | 7/1957 | Ketchledge | |
| 3,955,706 A * | 5/1976 | Whitaker | B65D 25/00 220/87.1 |
| 5,947,295 A * | 9/1999 | Lutin | B65F 1/062 220/495.07 |
| 5,954,958 A * | 9/1999 | Folden | A61M 1/882 210/764 |
| 8,109,409 B1 | 2/2012 | MacMurray | |
| 2003/0226773 A1* | 12/2003 | Shaffer | B65F 1/0006 206/204 |
| 2006/0081632 A1* | 4/2006 | Shieh | B65F 7/00 220/87.1 |
| 2007/0065053 A1* | 3/2007 | Feinberg | B65F 1/0006 383/105 |
| 2009/0017710 A1 | 1/2009 | Bugada et al. | |
| 2011/0217201 A1 | 9/2011 | Jensen et al. | |
| 2012/0315240 A1* | 12/2012 | Alper | C08F 242/00 424/78.18 |

OTHER PUBLICATIONS

International Search Report and Written Opinion for International Application No. PCT/US2021/54119, filed Oct. 8, 2021, dated Jan. 21, 2022, 10 pages.

* cited by examiner

DISPOSABLE PAD FOR INDOOR AND OUTDOOR GARBAGE CANS

CROSS-REFERENCE(S) TO RELATED APPLICATION(S)

This present application claims priority on U.S. Provisional Patent Application Ser. No. 63/089,803, filed on Oct. 9, 2020 and entitled Disposable Pad for Indoor and Outdoor Garbage Cans, the entire contents of which are hereby expressly incorporated by reference into the present application.

BACKGROUND OF THE INVENTION

1. Field of the Invention

The invention relates generally to indoor and outdoor garbage cans and, in particular, to a disposable pad or other piece of material that can be inserted into the garbage can to improve sanitization, reduce bacteria and germ growth, kill certain viruses, reduce odor, and absorb liquids in indoor and outdoor garbage cans.

2. Discussion of the Related Art

Despite best efforts to keep areas in and around garbage or trash cans clean, they inevitably get dirty. Oftentimes, trash bags associated with indoor garbage cans can repeatedly get dislodged from the can, which can cause food, beverages, and other waste to miss the bag and land directly into the bottom of the can. Additionally, garbage bags routinely break due to sharp ends of products deposited therein, overly loading the garbage bag, or uncareful removal of the bag from the can. When residue ends up in the bottom of the can, it oftentimes goes unnoticed. Other times, the residue is detected, but not immediately cleaned because it is unpleasant, inconvenient, and time consuming. This can cause bacteria to grow, germs and viruses to spread, and odors to permeate in and around the garbage can. Other times, the can is cleaned by a user with strong chemicals, which results in undesirable direct exposure to the user.

Many of the same issues are present with outdoor garbage cans. For instance, even when a garbage bag from an indoor can breaks, users nevertheless throw the broken bag directly into the outdoor garbage can, causing the contents of the bag to fall out of the bag and into the bottom of the outdoor can. Similarly, animals smelling food or other waste products can rip open bags causing the contents to fall out. Additionally, certain waste materials are exclusively deposited into an outdoor can, including pet waste and other chemical materials. This causes the smell associated with outdoor garbage cans to usually be even worse than indoor garbage cans. Further still, depending on the climate, outdoor cans may be exposed to excessive heat, and sometimes extended exposure to direct sunlight. This can exaggerate the undesirable smell and bacteria and germ growth and spread of viruses. In addition to the displeasure associated with smelly and gross garbage cans, there is concern for growth of bacteria, and other microorganisms that can be dangerous for humans and animals living in close proximity to the garbage can.

What is therefore needed is a disposable pad or other piece of material that can be deposited within an indoor or outdoor garbage or trash can. What is further needed is a disposable pad or other piece of material that is configured to kill germs and sanitize an indoor or outdoor garbage can. What is further needed is a pad or other piece of material that is configured to prevent growth of bacteria, germs, odor, spread of germs, and other undesirable contents within an indoor or outdoor garbage can. What is further needed is a pad or piece of material that has superior absorbable qualities in order to absorb any liquids or moisture contained within a garbage can.

SUMMARY AND OBJECTS OF THE INVENTION

By way of summary, the present invention is directed to a sanitization product for a garbage can that includes a disposable pad configured to be deposited into a base of the garbage can and a solution applied to the disposable pad to improve the characteristics of the interior of the garbage can. The solution may be configured to serve a number of purposes, including killing bacteria and germs within the garbage can, preventing exposure to microorganisms and spread of viruses, minimizing odor, and absorbing moisture or liquids. For instance, the solution may be a broad spectrum disinfectant, cleaner, virucidal, and deodorizer. The pad may be made of paper, cardboard, or foam material. Alternatively still, the pad can be made of a meltblown fabric. Additionally, the pad may comprise a deodorizer and it may also be scented to help minimize adverse smells.

According to another aspect of the present invention, a first disposable pad having a first solution is configured for use with an indoor garbage can, and a second disposable pad has a second solution that is configured for use with an outdoor garbage can. The first disposable pad may have a first area, whereas the second disposable pad may have a second area. The second area may be greater than the first area. Further still, the first disposable pad may be dimensioned to provide a protective liner for the bottom of the indoor garbage can. Additionally, the second disposable pad may be dimensioned to provide a protective liner for the bottom of the outdoor garbage can.

According to another aspect of the invention, a method of using a sanitization product for a garbage can is provided. The method may include the steps of inserting a disposable pad into a bottom of the garbage can, inserting garbage into the garbage can, and disposing of the garbage and the disposable pad. The method may also include the steps of attaching a first garbage bag to the indoor garbage can where the pad is located beneath, removing the first garbage bag once the first garbage bag is full, attaching at least one additional garbage bag to the indoor garbage can when the pad is located beneath, and disposing of the at least one additional garbage bag and the disposable pad. Additionally, the method may include the step of providing a plurality of disposable pads. Further still, the method may include the step of cutting the disposable pad to a desired size. While the pads shown in the current figures are shown to be generally rectangular in shape, the pads could come in any number of shapes, including those that mimic the shape of the bottom of the garbage can. Similarly, while a single sized pad is shown, pads could come in any number of different dimensions based on the shape of the garbage can and the desires of the user.

According to yet another aspect of the invention, a sanitization kit is provided for at least one garbage bag. The kit may include a sanitization solution configured to reduce bacteria and odor and spread of viruses and a first plurality of disposable pads coated in the sanitization solution. The first plurality of disposable pads may be placed within the garbage can. The first plurality of disposable pads may comprise fifty-two disposable pads, although smaller or larger packs of pads could similarly be provided. The kit may also provide a second plurality of disposable pads. Further still, the first plurality of disposable pads may have a first footprint configured for insertion into an indoor garbage can and the second plurality of disposable pads has a second footprint configured for insertion into an outdoor garbage can.

These, and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

Figure 1:
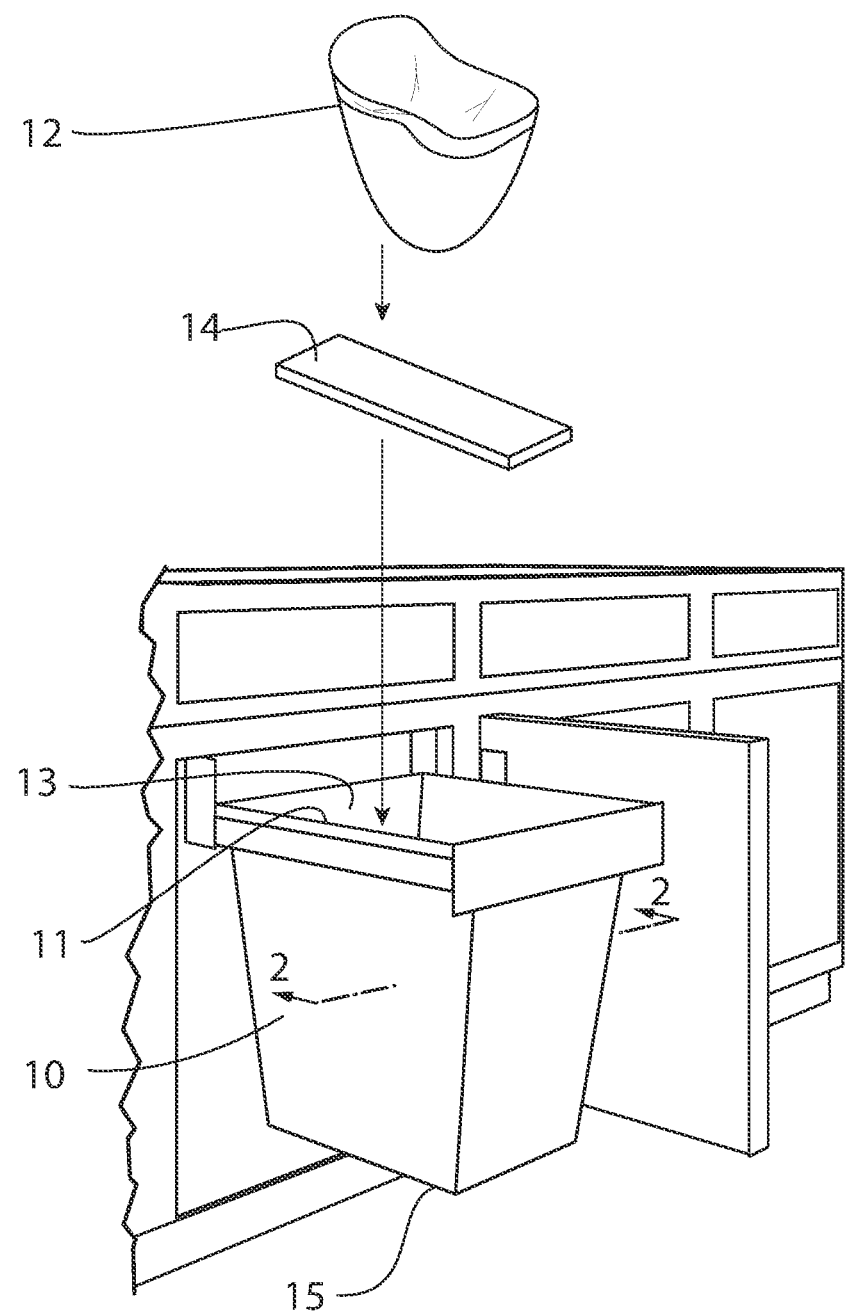
FIG. 1 illustrates an indoor garbage can with an inventive disposable pad.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected, attached, or terms similar thereto are often used. They are not limited to direct connection but include connection through other elements where such connection is recognized as being equivalent by those skilled in the art.

DESCRIPTION OF PREFERRED EMBODIMENTS

The present invention and the various features and advantageous details thereof are explained more fully with reference to the non-limiting embodiments described in detail in the following description.

The present invention is directed to a variety of different disposable pads or other materials that can be deposited into a garbage or trash can in order to improve the conditions of the interior of the garbage can. For instance, the pad or other material can serve one of many functions, including, minimizing growth and spread of bacteria, viruses, and germs, minimizing odors associated with the interior of the garbage can, improving the sanitization conditions of the interior of the garbage can, reducing exposure of microorganisms, absorbing liquids and moisture contained within the interior of the garbage can, and the like. The pad can also function to improve the conditions of the interior of the garbage can in any other desirable way. In practice, the pad or other material can be disposed of on a regular basis, for instance, on a weekly basis when garbage is collected. Of course, pads could be kept for multiple weeks depending on the needs of a given user, especially for an indoor garbage can that may get less dirty than and outdoor garbage can. As such, the pads help keep the interior of the garbage can clean.

Figure 2:
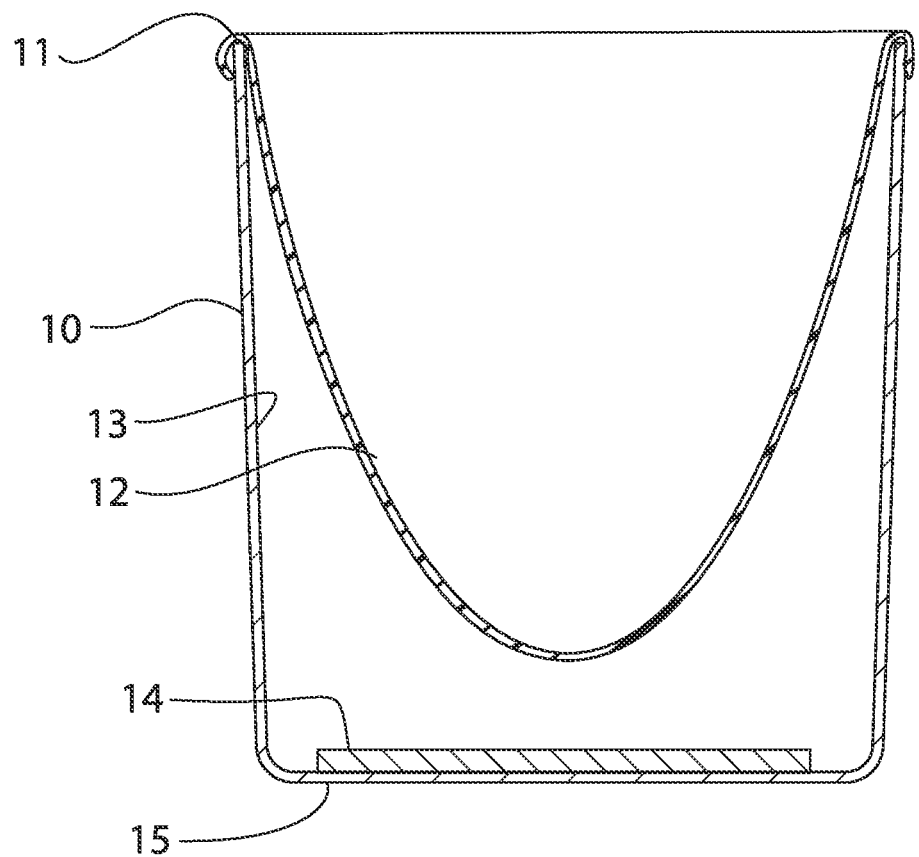
FIG. 2 illustrates a cross sectional view of an indoor garbage can with an inventive disposable pad.
Figure 3:
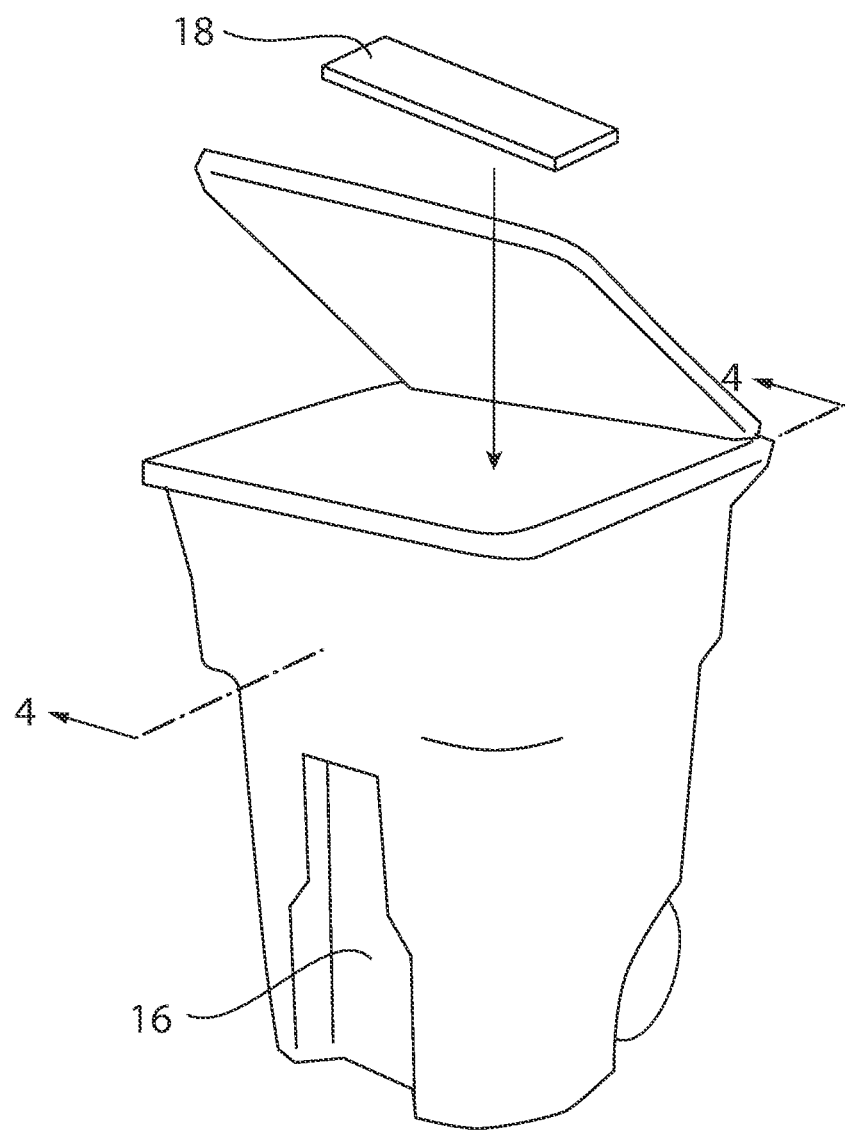
FIG. 3 illustrates an outdoor garbage can with an inventive disposable pad.
Figure 4:
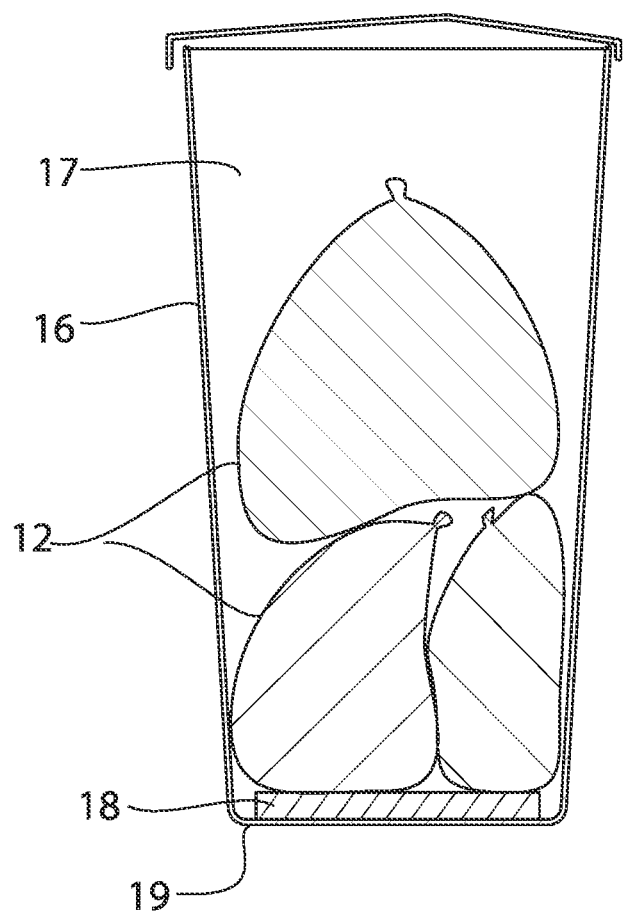
FIG. 4 illustrates a cross sectional view of an outdoor garbage can with an inventive disposable pad.

Different pads or other materials can be used depending on whether the pad is designed for use with an indoor garbage can or an outdoor garbage can. As known to those having ordinary skill in the art, many indoor garbage cans 10 are smaller in size, and typically have a bag 12 that is installed to the perimeter 11 of the opening of the can as shown in FIG. 1. Thus, for indoor garbage cans 10, the pad 14 or other material would be inserted into the interior 13 of the can 10 so it rests upon the bottom or base 15, after which bags 12 may be installed to the can 10. The pad 14 or other material may be dimensioned to securely fit within the bottom of the indoor garbage can 10 without significantly compromising the volume of garbage that can be received within the bag 12, as best seen in FIG. 2. In contrast, many outdoor garbage cans 16, particularly at home residences, such as what is shown in FIGS. 3 and 4, do not have individual bags attached thereto.

Rather, bags from indoor garbage cans 10 are deposited within the outdoor garbage can 16 until a waste removal company comes and retrieves the garbage bags, typically on a weekly basis. Thus, outdoor garbage cans 16 usually have a significantly larger volume so that they can receive multiple bags 12 that are collected over the course of a week. The pad 18 or other material for the outdoor garbage can 16 be larger to accommodate the larger footprint of the can 16 as seen in FIG. 4. Like the pad 14, the pad 18 is inserted into the interior 17 of the can 16 so it rests upon the bottom or base 19. Additionally, the various pads can be made of the same cardboard, paper, foam, or other material, but cut into different shapes depending on the size of the can it will be used with.

In one preferred embodiment, the pads 14, 18 are made of a meltblown fabric. Meltblown fabrics are made using a melt-blowing process which melts down polypropylene resin and blows the melted polymer into continuously and randomly laid fibers. Meltblown fabrics maintain their strength even when they become wet. This makes meltblown fabrics well suited for the present invention, where the pads 14, 18 will have a solution applied thereto, and where the pads 14, 18 will routinely get wet from the contents of the various cans 10, 16. Additionally, meltblown fabrics offer superior absorbable qualities. For instance, meltblown fabrics are capable of absorbing up to twelve times the dry weight of the meltblown fabric pad. Further still, meltblown fabrics have a high BTU value for potential incineration. Also, meltblown fabrics can soak up a variety of different materials without breaking down or having other adverse reactions, including for most hazmat, acidic, or caustic spill materials.

Furthermore, outdoor garbage cans 16 oftentimes receive other undesirable materials that users would never want in their home, including pet waste, chemicals, and the like. In contrast, many indoor garbage cans 10 are reserved only for certain materials, including food waste, tissues, napkins, and other cleaning materials. As a result, a pad 14 for use with an indoor garbage can 10 does not necessarily have the same requirements as a pad 18 for use with an outdoor garbage can 16.

Furthermore, a solution that is applied to the pad 14, 18 can vary depending on whether it will be used with an indoor garbage can 10 rather than an outdoor garbage can 16, More specifically, the solution applied to a pad 14 for an indoor garbage can 10 can be a weaker solution, whereas the solution applied to a pad 18 for an outdoor garbage can 16 can be a stronger solution. Additionally, pads 14, 18 having different solutions may be available depending on the specific desires of a consumer. If the primary concern is to prevent growth of bacteria and thus to improve sanitary conditions within the can, a first solution can be used. If reduction of odors from within the can is the primary concern, a second solution including a deodorizer can be used. Additionally or alternatively, the solution may scented so as to help overcome appealing smells. For instance, a specific solution may be used on pads 18 used with outdoor garbage cans 16 to deodorize food waste where the can 16 is located in areas where wild animals may be prevalent that open cans for leftover food waste. If concerns for both bacteria and odor apply, a third solution can be used. A separate solution can be used for outdoor garbage cans 16 owned by pet owners who deposit animal waste bags directly into the can 16. Of course, solutions can also be used that address all of the above-mentioned concerns simultaneously. Additionally, a separate solution may be used for cans 10, 16 that routinely have large quantities of food waste, for instance, for use at restaurants. The solution may be configured such that it successfully addresses any of the issues outlined above, while also being safe for a human to contact. As such, a human can pick up the pad and deposit it into the garbage can without being exposed to harmful chemicals or wearing gloves. Additionally, a human can hold the pad and cut it if a different size is desired so that it ideally fits within the can 10, 16.

In one preferred embodiment, the solution used for the pads 14, 18 is MY-SHIELD® Multi-Purpose, One Step Broad Spectrum Disinfectant Cleaner/Virucidal/Deodorizer. Exhibits A and B are attached here are hereby expressly incorporated by reference into the present application. This solution may include Alkyl Dimethyl Benzyl Ammonium Chloride, Octyl Decyl Dimethyl Ammonium Chloride, Dioctyl Dimethyl Ammonium Chloride, Didecyl Dimethyl Ammonium Chloride, Poly(hexamethylenebiguanide) hydrochloride, (3-Trimethoxysilyl) Propyl dimethyloctadecyl ammonium chloride, and other ingredients. While the Exhibits disclosure specific proportions of the active ingredients, these proportions can be altered depending on the results a given user desires for the inventive pads 14, 18 once the solution has been applied.

Further, different pads 14, 18 can be used depending on the garbage can 10, 16 in which it will be used. For instance, for garbage cans 10, 16 having a significant risk of accumulation of moisture, a thicker, more absorbent pad 14, 18 may be used. Additionally, pads 14, 18 may be selected based on the size and shape of the garbage can 10, 16. For instance, the pad 14, 18 may be configured to fit securely within the can 10, 16 as seen in FIGS. 2 and 4. More specifically, the pad 14, 18 may come in the size and shape of the footprint of traditional garbage can sizes, including substantially square pads, substantially rectangular pads, substantially circular pads, substantially oval-shaped pads, and the like. In this way, the pad 14, 18 may be configured to cover the entire bottom or base 15, 19 of the garbage can 10, 16 in order to prevent materials from getting beneath the pad 14, 18. Thus, the pad 14, 18 can serve as a protective liner to the interior 13, 17 of the garbage can 10, 16.

Additionally, the present invention may come in a convenient package for ongoing use. For instance, a pack may be provided that contains a set amount of pads. For instance, the pack may include four pads, such that a user can use one pad per week for one month. Similarly, the pack may include a dozen pads, which could be sufficient for a three-month supply of pads where the pads are disposed on a weekly basis, although some pads may be kept for multiple weeks. Further, the pack may include a six-month supply of pads. Further still, the pack may include a one-year supply of pads. Of course, the pads could also be sold individually, otherwise they can be sold in any desired quantity to improve ease of use. The pack may also include multiple types of pads, for instance a first set of pads for an indoor garbage can or cans, and a second set of pads for an outdoor can or cans. Additionally, the pack may include a mount to enable the pack to the be secured on or in close proximity to the designated garbage can. Alternatively still, the pack may come with pads and the solution in a bottle such that a user can apply the solution to the pad. Also, the pad and/or the pack may come equipped with various text and graphics to help users understand the purpose and characteristics of the pad and/or the pack. For instance, a logo, slogan, and/or instructions may be printed or otherwise affixed to the pad and/or the pack.

While the above description provides a number of potential uses of the pad, it should be noted that there are virtually innumerable uses for the present invention, all of which need not be detailed here. For instance, although the pads are described for use with garbage cans, they could similarly be used with other types of containers and devices. All the disclosed embodiments can be practiced without undue experimentation.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept. In addition, the individual components need not be fabricated from the disclosed materials, but could be fabricated from virtually any suitable materials.

Moreover, the individual components need not be formed in the disclosed shapes, or assembled in the disclosed configuration, but could be provided in virtually any shape, and assembled in virtually any configuration to improve the efficiency and functionality of the pads. Furthermore, all the disclosed features of each disclosed embodiment can be combined with, or substituted for, the disclosed features of every other disclosed embodiment except where such features are mutually exclusive.

It is intended that the appended claims cover all such additions, modifications and rearrangements. Expedient embodiments of the present invention are differentiated by the appended claims.

What is claimed is:

1. A sanitization product for a garbage can having one or more garbage bags located therein comprising:
   a disposable pad configured to be deposited into the interior of the garbage can beneath the one or more garbage bags; and
   a solution applied to the disposable pad to improve the characteristics of the interior of the garbage can;
   wherein the solution is configured to kill at least one of bacteria, germs, microorganisms, and viruses within the garbage can.

2. The sanitization product for a garbage can of claim 1, wherein the solution is configured to prevent exposure to microorganisms.

3. The sanitization product for a garbage can of claim 1, wherein the solution is configured to minimize odor within the garbage can.

4. The sanitization product for a garbage can of claim 1, wherein the disposable pad is configured to absorb moisture and liquid.

5. The sanitization product for a garbage can of claim 1, wherein the disposable pad is made of a meltblown polypropylene resin material.

6. The sanitization product for a garbage can of claim 1, wherein the pad further comprises a deodorizer.

7. A sanitization product for a garbage can comprising:
   a disposable pad configured to be deposited into the interior of the garbage can; and
   a solution applied to the disposable pad to improve the characteristics of the interior of the garbage can,
   wherein a first disposable pad having a first solution is configured for use with an indoor garbage can and a second disposable pad having a second solution is configured for use with an outdoor garbage can;
   wherein the first disposable pad has a first area;
   wherein the second disposable pad has a second area; and
   wherein the second area is greater than the first area.

8. The sanitization product for a garbage can of claim 6, wherein the first disposable pad is dimensioned to provide a protective liner for the bottom of the indoor garbage can.

9. The sanitization product for a garbage can of claim 6, wherein the second disposable pad is dimensioned to provide a protective liner for the bottom of the outdoor garbage can.

10. The sanitization product for a garbage can of claim 7, wherein the disposable pad is made of a meltblown polypropylene resin material.

11. A sanitization kit for at least one garbage can comprising:
    a sanitizing solution configured to reduce bacteria and odor;
    a first plurality of disposable pads coated in the sanitization solution; and
    a second plurality of disposable pads;
    wherein the first plurality of disposable pads is placed within a first garbage can.

12. The sanitization kit of claim 11, wherein the first plurality of disposable pads comprises at least a dozen pads.

13. The sanitization kit of claim 11, wherein the first plurality of disposable pads has a first footprint configured for insertion into an indoor garbage can; and
    wherein the second plurality of disposable pads has a second footprint configured for insertion into an outdoor garbage can.

14. The sanitization kit of claim 11, wherein the first plurality of disposable pads and the second plurality of disposable pads are made of a meltblown polypropylene resin material.

15. A method of using a sanitization product for a garbage can comprising the steps of:
    inserting a disposable pad into an interior of the garbage can;
    inserting garbage into the garbage can; and
    disposing of the garbage and the disposable pad.

16. The method of claim 15, wherein the garbage can is an indoor garbage can; and further comprising the steps of:
    attaching a first garbage bag to the indoor garbage can where the pad is located beneath;
    removing the first garbage bag once the first garbage bag is full;
    attaching at least one additional garbage bag to the indoor garbage can where the pad is located beneath; and
    disposing of the at least one additional garbage bag and the disposable pad.

17. The method of claim 15, wherein the garbage can is an outdoor garbage can; and further comprising the steps of:
    placing the disposable pad in the bottom of the outdoor garbage can;
    placing at least one filled garbage bag on top of the disposable pad; and
    disposing of the at least one filled garbage bag and the disposable pad.

18. The method of claim 15, further comprising the step of providing a plurality of disposable pads.

19. The method of claim 15, further comprising the step of cutting the disposable pad to a desired size.

* * * * *